US008684946B1

(12) United States Patent
Sims et al.

(10) Patent No.: US 8,684,946 B1
(45) Date of Patent: Apr. 1, 2014

(54) METHOD AND APPARATUS FOR DETERMINING THE SENSITIVITY OF CONE PHOTORECEPTORS AND USES THEREOF

(75) Inventors: Janene Sims, Trussville, AL (US); Robert N. Kleinstein, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 212 days.

(21) Appl. No.: 11/641,169

(22) Filed: Dec. 19, 2006

Related U.S. Application Data

(60) Provisional application No. 60/751,741, filed on Dec. 19, 2005.

(51) Int. Cl.
*A61B 13/00* (2006.01)

(52) U.S. Cl.
USPC ............................................. 600/558; 351/246

(58) Field of Classification Search
USPC .................................. 600/558; 315/243, 246
See application file for complete search history.

(56) References Cited

U.S. PATENT DOCUMENTS 4,618,230 A * 10/1986 Ens et al. ...................... 351/221
2004/0143403 A1 * 7/2004 Brandon et al. ................ 702/19

OTHER PUBLICATIONS

Renner et al. "Photopigment optical densirt of the human foveola and a paradoxical senescent increase outside the fovea" Vis. Neuroscience 2004. pp. 1-9.*

Sample et al. "Progressive Color Visual Field Loss in Glaucoma" Investigative Ophthalmology & Visual Science vol. 13. May 1992. pp. 2068-2071.*
Anderson et al. "What limits detection and resolution of short-wavelength sinusoidal gratings across the retina?" Vision research (2002) p. 981-990.*
Karwatsky et al. "Red-Green Chromatic Mechanisms in Normal Aging and Glacomatous Observers" Investigative Ophthalmology & Visual Science. Aug. 2004. p. 2681-2682.*
Heron et al. "Central Visual Fields for Short Wavelength Sensitive Pathways in Glaucoma and Ocular Hypertension" Jan. 1988 Investigative Ophthalmology & Visual Science. p. 64-68.*
David Hubei Eye, Brain, and Vision. Ch4 4, p. 12. 1988.*
Hahn, "The Retina: gross anatomy", 1995, accessed at http://retina.anatomy.upenn.edu/~rob/lance/retina_gross.html.*

* cited by examiner

*Primary Examiner* — Max Hindenburg
*Assistant Examiner* — Renee Danega

(57) ABSTRACT

The present disclosure describes a psychophysical test to assess the cone photoreceptor pathway by determining the sensitivity of the cone photoreceptors. The test may be used to determine of a subject is suffering from, or is likely to suffer from, a disease state involving the fovea, parafovea, macula, neurological pathways used by these area to communicate with the visual processing centers in the brain and cone photoreceptors and/or ganglion cells. The present disclosure also describes an apparatus for such testing purposes. Using the novel cone photoreceptor sensitivity test and apparatus, the present disclosure shows that cone photoreceptor sensitivity in subjects with primary open angle glaucoma was decreased as compared to a control group (p=0.04). This cone photoreceptor sensitivity test is shown to have excellent repeatability, can be administered in a short time, does not require extensive subject instruction and meets other limitations required for application in a clinical setting.

26 Claims, 6 Drawing Sheets

METHOD AND APPARATUS FOR DETERMINING THE SENSITIVITY OF CONE PHOTORECEPTORS AND USES THEREOF

This application claims priority to and benefit of U.S. Provisional Patent Application No. 60/751,741 filed Dec. 19, 2005.

STATEMENT REGARDING FEDERAL FUNDING

The US Government has a paid-up license in this invention and the right in limited circumstances to require the patent owner to license to others on reasonable terms as provided for by the terms of grant nos. EY08893 & EY010419 awarded by the National Institute of Health, National Eye Institute.

FIELD OF THE DISCLOSURE

The present disclosure relates to methods and apparatus for the determination of function of the cone photoreceptor pathway by determining the sensitivity of the cone photoreceptors. The methods and apparatus may be used in the diagnosis of a variety of diseases states and conditions in a subject and/or for the identification of subjects who are at-risk for such disease states and conditions.

BACKGROUND

The human macula comprises a small cone-dominated fovea surrounded by a parafovea area. The function of the rod and cone photoreceptors is impacted by the physiology of the macula, which can be impacted by many disease states and conditions which interrupt normal macular physiology. By determining the function of the cone photoreceptor pathway, the function and physiology of the eye can be monitored. When the cone photoreceptor pathway functions normally, this suggests that no disease state and condition is present (or if present, are at a very early stage) which effect the macula, fovea, parafovea or the neurological pathways transmitting information from these regions to visual processing centers in the brain.

Conversely, when the function of the cone photoreceptor pathway is abnormal, this suggests a disease state or condition is present which impact the macula, fovea, parafovea or the neurological pathways transmitting information from these regions to visual processing centers in the brain, which is manifesting itself as an alteration in cone photoreceptor function. The prior art has taught methods for determining if a subject is suffering from impaired cone photoreceptor pathway function. However, many such methods are cumbersome and time consuming to administer and many lack the specificity and sensitivity of the methods of the present disclosure.

The art is lacking is a method to determine impaired cone photoreceptor pathway function, which produces high test-retest reliability and reproducibility, which can be administered in the clinical setting with decreased burden on the subject and the healthcare provider, and which is simple to administer. The present disclosure provides an apparatus and method for determining cone photoreceptor pathway function by analyzing the responses of the cone photoreceptors as a means to determine if a subject is suffering from or at risk for a disease state or condition which effects the macula, fovea, parafovea or the neurological pathways transmitting information from these regions to visual processing centers in the brain. An exemplary device for carrying out this analysis is also described. The subjects identified with impaired cone photoreceptor pathway function can then be evaluated such disease states or conditions. The disease states include, but are not limited to, age-related macular degeneration, glaucoma, and diabetic retinopathy, among others, as well as other disease state or condition that impact the macula and/or the central vision of the eye. In one embodiment, the disease state or condition is glaucoma. In a specific embodiment, the glaucoma is primary open angle glaucoma (POAG). For example, patients with impaired cone photoreceptor pathway function can be monitored for increased risk of a disease state, such as, but not limited to, glaucoma. In addition, patients identified with such disease states can be monitored to track disease progression and the like. Furthermore, such individuals may be started on early intervention strategies to prevent or delay the progression or onset of the disease state and the effectiveness of such intervention strategies can be monitored.

DETAILED DESCRIPTION

Figure 1A:
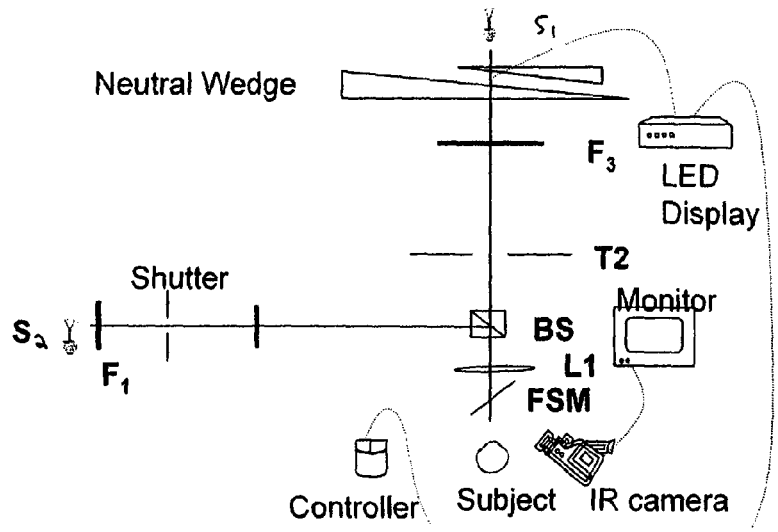
FIG. 1A shows one embodiment of the apparatus used in the described foveal sensitivity test.

The present disclosure describes a new method for the measurement of cone photoreceptor pathway function to identify subjects who have impaired cone photoreceptor function and who are suffering from or at-risk for developing a variety of disease states and conditions. The method can be administered in, a short time (in as little as 30 minutes or less) in the clinical setting. As a result, healthcare providers will be able to offer the test on a practical and affordable basis, making application of the test and realization of its benefits more widespread. In addition, the burden the test imposes on the subject and the healthcare provider will be significantly reduced. Furthermore, the subject need not have prior exposure to psychophysical test methods.

In addition to its use as a diagnostic tool and/or a tool to monitor treatment effectiveness and disease progression, the method described herein could be used to identify impaired visual function associated with impaired cone photoreceptor pathway function resulting from the structural, biochemical and physiological changes responsible for the impaired visual function and the progression of the disease states associated with cone photoreceptor function, such as, but not limited to, glaucoma. By the early and accurate identification of those individuals at risk for developing glaucoma and the other disease states discussed herein (by virtue of their identification as having impaired cone photoreceptor pathway function) the structural, biochemical and physiological changes could be identified and correlated with various stages of disease state progression. Such information can be used to design theoretical models of the disease state, evaluate animal models of the disease state and to identify new opportunities for therapeutic intervention in the treatment of the disease state.

The present disclosure presents glaucoma as an exemplary disease state to be studied using impairment of cone photoreceptor pathway function in a subject. However, the method of determining such impairment of cone photoreceptor pathway function is applicable to the other disease states discussed herein.

The present disclosure shows that foveal sensitivity, as determined by cone photoreceptor function, is shown to be impaired in subjects suffering from glaucoma. This impairment of cone photoreceptor pathway function is observed prior to major structural and physiological damage caused by the glaucoma process. Therefore, by monitoring the health of the cone photoreceptors, those individuals suffering from or at-risk for glaucoma can be identified. This earlier detection will result in the initiation of preventive measure, increased monitoring and/or early initiation of treatment before significant impairment of vision occurs. As a result, the most significant aspect of glaucoma-related vision impairment may be prevented or delayed.

General Description of Test Parameters

A general description of the test method disclosed is given below. In the method described, foveal sensitivity is measured by determining cone photoreceptor function using a device as described herein. The general test method described may be used with the variations described herein. The present method is a psychophysical method which comprises presenting a target to the eye using a Maxwellian view optical system. The test utilizes two optical beams, one a flashing stimulus and the other a steady background, brought together by a beam splitter in Maxwellian view. The Maxwellian view optical system produces a target image on a desired section of the fovea. The Maxwellian view optical system may comprises components to control and/or vary the wavelength of the target image, the wavelength of the adapting field, the luminosity of the target image, the luminosity of the adapting field, the temporal pattern (flash pattern) of the target image, the position of the target image and the size of the target image. Visual parameters for the subject to be tested are evaluated using methods known to those of ordinary skill in the art. A variety of parameters may be evaluated for a given subject. These parameters include, but are not limited to, visual acuity, color vision, intraocular pressure (IOP), optic nerve appearance, visual field defects and the like. These parameters may be used by the caregiver in assessing the ocular health of the subject in conjunction with the results of the test method described herein. Prior to initiating the test procedure, the subject's eye may be dilated using methods well known to those of ordinary skill in the art. In addition, the subject's visual acuity may be corrected prior to initiating the testing procedure.

The subject is placed in the apparatus so that the subject's eye (including the fovea) remains stationary during the procedure. This may be accomplished using a dental impression mounted to a bite bar or using other methods known to those of ordinary skill in the art. The position of the subject's eye may be monitored using an optical device, such as, but not limited to, an infrared camera to verify the subject's eye remains stationary during testing. As only one eye at a time is subject to the testing method during a given session, the eye not being tested may be covered during testing.

During the testing procedure, the subject is presented with a fixation target. The fixation target is presented on a larger adapting field which serves as the background. The subject is instructed to look at the center of the fixation target. The subject's eye may be aligned with the fixation target so that the foveal center is in alignment with the fixation target by adjustment of the fixation target in the x, y and/or z axes or adjustment of the subject's eye in the x, y and/or z axes. In one embodiment, the fixation target is a square formed by four cross hairs. In this embodiment, the subject is instructed to look at the center of the square.

After subject alignment, a target image is presented to the subject during testing. A target image is presented to the subject against the adapting field. The adapting field is designed to saturate the rod photoreceptor cells while the target image is designed to stimulate the cone photoreceptor cells. The target image is presented to the subject in a predefined sequence to measure the sensitivity of the cone photoreceptor cells. The predefined sequence may be varied as desired by the user. In one embodiment, the target image is presented initially in the center of the fixation target, which corresponds to the foveal center of the subject. The target image may be subsequently presented at different positions on the fovea, parafovea or macula in relation to the foveal center to determine cone photoreceptor sensitivity in a desired area of the eye. In one embodiment, the target image is presented at different locations within the fovea; in an alternate embodiment, the target image is presented at different areas of the fovea and/or parafovea; in yet another embodiment, the target image is presented at different areas of the fovea, parafovea and/or macula. In one embodiment, the target image is moved in the horizontal meridian of the subject's eye in both the temporal and nasal direction, in increments to determine cone photoreceptor sensitivity. The increments may be selected by the healthcare provider administering the test such that points representing the entire fovea, parafovea, and or macula are tested. In one embodiment, the increments are selected to span the distance from the foveal center, or foveola, to the foveal periphery. In one embodiment, the increments are from 0.1 to 0.4 degrees; the increments may be the same or the increments may be varied. In one specific embodiment for testing cone photoreceptor function in the fovea, the increment is 0.26 degrees and the subject is presented with the test image at the foveal center (0 degrees) and at positions of 0.26 degrees, 0.55 degrees and 0.88 degrees (representing the foveal periphery) from the foveal center in the horizontal meridian in both the nasal and temporal direction. Therefore, the target image is presented to the subject 7 times in this embodiment. As would be obvious to one of ordinary skill in the art, the order of presentation of the target image may be varied and is not required to proceed in a step-wise manner as described above. Furthermore, when it is desired to test areas of the parafovea or macula the positions tested may be expanded as would be known to one of ordinary skill in the art.

As discussed above, the fovea has the highest concentration of cone photoreceptors. The density of the cone photoreceptors is greatest at the foveal center (foveola) and decreases as one proceeds away from the foveal center. In addition, the distribution of the various subtypes of cone photoreceptor cells may also vary as a function of position within the fovea, parafovea or macula and may therefore be examined by varying the parameters of the test, such as but not limited to, the position of the test image. There are generally three distinct types of cone photoreceptors recognized: (i) the blue cone photoreceptors which are responsive to shorter wavelengths of light (generally 400 to 500 nm); (ii) the green cone photoreceptors which are responsive to intermediate wavelengths of light (generally 500 to 600 nm); and (iii) the red cone photoreceptor which are responsive to longer wavelengths of light (generally 600 to 750 nm). Therefore, varying the position of the target image allows assessment of cone photoreceptor sensitivity in various parts of the eye to be determined and allows the sensitivity of specific types of cone photoreceptors to be determined.

The target image is presented to the subject either in a continuous mode, or a flashing mode. In the flashing mode, the duration of the flash may be from 1/5 of a second to 1/100 of a second. In a specific embodiment, the duration of the test flash is 1/20 of a second every second. Furthermore, the temporal delay between flashes may be varied from 10 to 100 milliseconds. The size of the target image may be selected by the healthcare professional administering the test. In one embodiment, the target image is from 5 minutes to 30 minutes. In a specific embodiment, the target image covers 13 minutes. The shape of the target image may be any shape desired. However, in a specific embodiment, the shape of the target image is circular.

For each presentation of the target image, the subject determines at what point the target image is no longer visible to the subject as the luminosity of the adapting field is altered. The subject may manually adjust the luminosity of the adapting field or the luminosity of the adapting field may be controlled automatically by the healthcare provider administering the test. The change in luminosity occurs in defined increments. The defined increments may be from 0.05 to 2.0 log units. In one specific embodiment, the increment is 0.1 log units. In one embodiment, a starting luminosity of the adapting field is selected such that every subject, irrespective of cone photoreceptor sensitivity, can see the target image. The initial luminosity of the adapting field in this embodiment may be from 0.1 to 0.8 $cd/m^2$. The luminosity of the adapting field is increased in defined increments as discussed above until the subject indicates the target image is no longer visible. The point at which the subject indicates the target image is no longer visible is the endpoint measurement for the given target image. The process may be repeated as many times as desired at a given location for the target image to obtain a plurality of endpoint measurements for a given target image location. The plurality of endpoint measurements may be used independently or may be averaged to yield an averaged endpoint measurement. In an alternate embodiment, a starting luminosity of the adapting field is selected such that every subject, irrespective of cone photoreceptor sensitivity, cannot see the target image. The luminosity of the adapting field is decreased in defined increments as discussed above until the subject indicates the target image becomes visible. The point at which the subject indicates the target image is visible is the endpoint measurement for the given target image. The process may be repeated as many times as desired at a given location for the target image to obtain a plurality of endpoint measurements for a given target image location. The plurality of endpoint measurements may be used independently or may be averaged to yield an averaged endpoint measurement. The process above for obtaining endpoint measurements is repeated for every location of the target image. In the embodiment discussed above where 7 target image locations are used, a total of at least seven endpoint measurements would be obtained.

Various factors regarding the endpoint measurement may be recorded for future analysis, such as, but not limited to, the luminosity of the adapting field (both at initiation and at determination of the endpoint measurement), the wavelength of the adapting field, the luminosity of the target image, the wavelength of the target image, the size of the target image, the position of the target image and the time taken for the subject to reach the endpoint measurement.

The subject's response to the target image is used to determine an "endpoint measurement" which is an indicator of cone photoreceptor sensitivity and therefore cone photoreceptor function. The endpoint measurement may then be used to determine the subject's disease status. If the cone photoreceptor function is impaired, the subject is deemed to have a positive disease status. As used herein positive disease status indicates the subject is suffering from, or at risk for, a disease state or condition, such as, but not limited to, glaucoma and the other disease states or conditions described herein. If the cone photoreceptor function is not impaired, the subject is deemed to have a negative disease status. As used herein negative disease status indicates the subject is not suffering from, or is not currently at risk for, a disease state or condition, such as, but not limited to, glaucoma and the other disease states or conditions described herein. The endpoint measurement may be used directly to determine a subject's disease status. Alternatively, the endpoint measurement may be compared with similar measurements in a comparative database to determine the subject's disease status. In a further alternate embodiment, the endpoint measurement may be used in a model of a particular disease state in order to determine the subject's disease status.

As discussed herein, the method of the present disclosure is designed to stimulate the cone photoreceptors and ganglion cells, with no or minimal stimulation of the rod photoreceptor cells. The function of the adapting field is to saturate the rod photoreceptor cells so that they do not contribute or do not contribute significantly to the foveal sensitivity measured by the disclosed method. In one embodiment, at least 70% of the rod photoreceptor cells are saturated; in an alternate embodiment, at least 80%, 90%, 95%, 99% or 100% of the rod photoreceptor cells are saturated. As used herein, "saturated" means that population of rod photoreceptor cells does not contribute to the foveal sensitivity measured by the disclosed method. The brightness (luminosity) and/or the wavelength of the adapting field may be adjusted to accomplish this function. The adapting field may be produced by any acceptable light source, hereinafter referred to as the first light source. In one embodiment, the first light source is a tungsten quartz halogen source. The luminosity of the first light source may be modulated through the use of a filter (often referred to as a neutral wedge filter in the art). By modulating the luminosity of the first light source, the luminosity of the adapting field may be varied; as a result, the stimulation of the rod photoreceptor cells may be modulated. The subject may modulate the luminosity of the first light source (and therefore of the adapting field) in response to a stimulus (such as the target image) or the luminosity of the first light source may be adjusted by a person administering the test or using a preset program. Alternatively, the wavelength of light used to create the adapting field may be varied in order to accomplish the function of the adapting field. In yet another approach, the luminosity and wavelength can be varied together to accomplish this function. In one embodiment, the first light source is modified by a first filter which transmits only a predetermined wavelength of the first light source (referred to herein as the "adapting field wavelength") to comprise the adapting field. In one embodiment, the adapting field wavelength is selected so as to saturate the rod photoreceptor response. In an alternate embodiment, the adapting field wavelength is selected based on the wavelength of light comprising the target image (referred to as the "target image wavelength", defined below).

The function of the target image is to stimulate the cone photoreceptor cells and/or the ganglion cells. The target image may be produced by any acceptable light source, hereinafter referred to as the second light source. In one embodiment, the second light source is a tungsten quartz halogen source. The luminosity of the second light source may be modulated as discussed above if desired. However, in one embodiment, the luminosity of the target image remains constant. If varied, the subject may modulate the luminosity of the second light source (and therefore of the target image) or the luminosity of the second light source may be adjusted by a person administering the test or using a preset program. The wavelength of light comprising the target image may also be varied. In one embodiment, the second light source is modified by a second filter which transmits only a predetermined wavelength of the second light source (referred to herein as the "target image wavelength") to comprise the target image. In one embodiment, the target image wavelength is selected so as to stimulate the rod photoreceptor response, or a response from a subset of rod photoreceptor cells. In an alternate embodiment, the target image wavelength is selected based on the adapting field wavelength.

In one embodiment, the adapting field wavelength and the target image wavelength are different from one another. For example, the adapting field wavelength may be 540 nm (so that the adapting field appears green) and the target image wavelength may be 600 nm or greater (so that the target image appears orange to red). Alternatively, the adapting field wavelength may be 620 nm (so that the adapting field appears yellow) and the target image wavelength may be 470 nm or greater (so that the target image appears blue). Other adapting field wavelengths and target image wavelengths may also be used as desired.

The endpoint measurements may be compared to a comparative database in making a determination of disease status. When the endpoint measurements are compared to a comparative database, the individuals in the comparative database may be aged matched to the subject, or may be non-aged matched as compared to the subject. For example, if the subject is 65 years of age, in one embodiment the comparative database may be composed of individuals with ages from 60 to 70 years, or in a second embodiment, the comparative database may be composed of individuals with ages from 25 to 40 years. The use of a comparative database comprising a younger population may offer certain advantages since the younger subjects that comprise the population will be more likely to be free of disease states and other conditions that may impact their cone photoreceptor sensitivity. As discussed above, most prior techniques for diagnosing individuals with glaucoma and other disease states are not sensitive enough to detect individuals with early stages of the disease states. Therefore, using an age matched population for the comparison may actually decrease the sensitivity of the method to identify impairments in the cone photoreceptor pathway as determined by measuring cone photoreceptor sensitivity since the age matched population of the comparative database may in fact have a certain degree of impaired cone photoreceptor sensitivity.

The individuals making up the comparative database may be healthy (i.e., disease free) or they may be selected based on their diagnosis with glaucoma or any of the other disease states which have impaired cone photoreceptor sensitivity as a clinical manifestation, or a combination of the foregoing. If healthy individuals are selected, the endpoint measurements determined from the subject can be compared with the corresponding endpoint measurements from the healthy individuals. If individuals with a diagnosed disease state are selected, the index factors determined from the subject can be compared with the corresponding index factors for the individuals diagnosed with a disease states and/or defined stages of a disease state. In this manner, the comparison may be able to predict if the subject has impaired cone photoreceptor sensitivity (from a comparison with healthy individuals in the comparative database), is suffering from a disease state (from a comparison with individuals in the comparative database diagnosed with said disease state) or to diagnose the severity of the disease state (from a comparison with individuals in the comparative database diagnosed with said stage of the disease state). For example, if the disease state is glaucoma, the endpoint measurements determined for the subject may be compared to corresponding endpoint measurements from individuals in the comparative database who are diagnosed with various stages of glaucoma.

The comparative database may be stratified based on a number of stratification criteria. These criteria may be risk factors, demographic factors, morphological factors, other relevant factors or a combination of the preceding. Examples, of risk factors include, but are not limited to, age, smoking status, body mass index, and status with regard to health conditions (for example diabetes). Other risk factors may also be included. Demographic factors include, but are not limited to, gender and ethnicity. Morphological factors include, but are not limited to, anterior segment anatomy, IOP, optic nerve head appearance, and corneal thickness. The inclusion of a specific stratification criteria as a risk factor, demographic factor or morphological factor may be modified (for example, age may be considered both a risk factor and a demographic factor). The individuals in the comparative database may be tagged or otherwise identified, such that the appropriate population of individuals in the comparative database may be selected for the comparison to the subject.

Furthermore, the comparative database may be refined over time. The individuals in the database may be followed over time and their health status monitored. If an individual no longer meets an inclusion criterion for the comparative database, the individual may be removed. The inclusion criteria may be development of a disease state or impaired foveal sensitivity within a defined time period of the inclusion of the individual in said comparative database.

General Description of the Apparatus

An instrument was created in order to administer the novel method for determining cone photoreceptor sensitivity. The instrumentation was adapted from a Stiles-Crawford apparatus described by Westheimer (17). The apparatus allows the administration of the cone photoreceptor sensitivity test in a non-invasive manner to assess the cone photoreceptor pathway. The apparatus comprises generally a first light source, which produces a first optical beam, a second light source, which produces a second optical beam, a beam splitter to join the first and second optical beams, a lens to image the collimated first and second beams on the subject's entrance pupil, a first and a second modifying element to modify the first optical beam, a third modifying element to modify the second optical beam and a fixation target, an element to maintain the subject's head in a fixed position and an element to adjust the position of the fixation target relative to the subject's eye.

The first and second light sources may be any commercially available light sources. The first and second light sources may produce white light or light of a specific wavelength. However, in one embodiment, the first and second light sources were tungsten quartz halogen light sources producing white light (Oriel Model #63941 lamps). The first optical beam produced by the first light source generates a continuous adapting field which serves as a background for the target image generated by the second optical beam produced by the second light source. The target image may be non-continuous (flashing). The first optical beam may be modified by the first and second modifying elements to impart desired characteristics to the first optical beam and therefore the adapting field. In one embodiment, the first modifying element controls the luminosity (intensity) of the adapting field and the second modifying element controls the wavelength of the light comprising the first optical beam and therefore the adapting field. The second optical beam may be modified by the third modifying element to impart desired characteristics to the second optical beam and therefore the target image. In one embodiment, the third modifying element controls the wavelength of light comprising the second optical beam. The first, second and third modifying elements may be controlled automatically in a pre-programmed manner, by the healthcare provider administering the test or by the subject. The first, second and third modifying element may be controlled in the same manner or through a combination of the foregoing. In one embodiment, the first modifying element is controlled by the subject and the second and third modifying elements are controlled by the healthcare provider administering the test or automatically. The first, second and third modifying elements may be filters designed to accomplish the purposes described. For example, a neutral wedge filter may be used as the first modifying element and a wavelength control filter may be used as the second and third modifying elements.

The element to maintain the subject's head in a fixed position may comprise any combination of elements known to accomplish this function in the art. In a specific embodiment, such element comprises a bit bar and a dental impression (specific to the subject) mounted to the bite bar. The element to adjust the position of the fixation target may comprise any combination of elements known to accomplish this function in the art. In a specific embodiment, such element comprises a fully adjustable stage capable of movement in the x, y and z axes. The apparatus may further comprise a shutter or similar device to regulate the display of the second optical beam produced by the second light source, a monitoring element to monitor the position of the subject's eye and other accessory devices common on apparatus used for psychophysical testing. In one embodiment, the element to monitor the position of the subject's eye comprises an infrared camera in communication with a monitor and a front silvered mirror.

Specific Description of Test Method

The following discussion describes a specific embodiment of the cone photoreceptor sensitivity test described above. The specific embodiment was used on subjects in order to determine the efficacy of the disclosed method. The following discussion is provided to be exemplary of the general test methods disclosed and should not be considered to limit the scope of the present disclosure to the specific method described.

Pre-Testing Evaluation

Informed consent was obtained for subjects with (n=16) and without (n=17) primary open angle glaucoma (POAG) in accordance with the Declaration of Helsinki. Subjects were recruited from the University of Alabama at Birmingham School of Optometry and the University of Missouri St. Louis College of Optometry clinics, and from a glaucoma specialist in private practice in the St. Louis, Mo. area. Separate approvals were obtained from the Institutional Review Boards of both Universities. Primary open angle glaucoma patients, 18 years and older without any other eye disease, were recruited to participate in this research. Records of complete eye examinations, including dilation within three months of enrolling in this study, were required. The inclusion criteria were healthy right eyes free of corneal, lenticular, optic nerve, media, and macular opacities and diseases and best corrected visual acuity (VA) of 20/25 or better. If these data were not available, a complete dilated eye exam was done to determine if the subject met the inclusion criteria. The color vision of the subject was also noted. Subjects meeting the inclusion criteria were invited to enroll in this study. Glaucoma patients free of other ocular diseases were recruited regardless of their stage of glaucoma.

The visual fields (VFs) of the glaucoma subjects enrolled in the study were evaluated. Hodapp's criteria were used to classify the glaucoma patients as mild, moderate, or severe stage of glaucoma (16). Automated visual fields were performed on normal subjects only if their confrontation VFs or the appearance of the optic nerve heads were abnormal.

The control group (without glaucoma) included 17 subjects, 12 females (70%) and 5 males (30%). Twelve African American subjects (70%) were enrolled in this group. The remaining five subjects (30%) were Caucasian. The mean age was 48.1 years+12.3 years with a median age of 52 years. This group was about 11 years younger than the POAG group primarily because most of the older subjects without glaucoma willing to participate had other eye diseases making them ineligible. Cataracts were the number one cause for study ineligibility for potential subjects without glaucoma. Very few of these subjects had a positive family history of glaucoma. Only three of them (17%) reported either a grandparent, aunt, or uncle was diagnosed with glaucoma.

The POAG group (with primary open angle glaucoma) included 16 individuals, 11 males (69%) and 5 females (31%). Eighty-one percent of this group was Caucasian, and 19% were African American. The mean age for this group was 59.1±11.4 years with a median age of 61 years. There were 21 reports of a family member with glaucoma. This number is larger than the number of members in this group because more than one family member could be listed. Five subjects (31%) had two or more family members with glaucoma. Nine of the 16 patients (56%) of the POAG group reported a negative family history of glaucoma. Parents of subjects accounted for 7/32 (22%) of the positive family history of glaucoma reports. The remaining positive reports were distributed between siblings (21%), children (5%), and grandparents, aunt, or uncle (5%).

Medical History

Health histories were taken for the participants in the study. The results are summarized in Table 1.47% of the control group and 43% of the POAG group reported a medical history positive for systemic hypertension. 17% of the control group reported a diagnosis of diabetes and elevated cholesterol levels, but none had cardiovascular disease. Diabetes and cardiovascular disease were present in only 6% of the POAG group. Elevated cholesterol was reported in 18% of the POAG group. Although the control group was younger than the POAG group, the occurrence of systemic disease was greater in the control group. Table 1 shows the percentage of systemic disease for both control and POAG groups, further subdivided based on ethnicity.

Visual Acuity

Because VA was part of the inclusion criteria for the study, the VAs of both groups were 20/25 or better in the right eye. On average the normal group was slightly better than the standard 20/20 Snellen acuity at 20/18, and the POAG group was slightly worse at 20/22.

Color Vision

The Ishihara color vision test was performed on the subjects prior to testing; however, color deficiencies did not preclude study participation. The subjects were required to be able to differentiate between the flash and the background. Only one of the normal patients (43-MM) failed the color vision test. Patient 43-MM had never been diagnosed with a red-green or blue-yellow color deficiency, but had noted that during the last year the subject's vision was not as sharp as normal even though the subject's VA (20/20) was unchanged from previous exams. Two of the POAG subjects (13-WR and 28-TC) had longstanding protonamolous deficiencies. All of the color deficient subjects were able to complete the study without any complications, but the duration of the test for 43-MM was longer than the duration for other subjects. There was no significant difference between the prevalence of red-green color vision problems in the POAG group compared to the control group.

Ocular Medications, Intraocular Pressures and C/D Ratio

A wide variety of topical medications was used to lower the IOP of patients with POAG. No subjects in the normal group were taking any eye medications. Twenty-five percent of the POAG group were taking two medications to control their IOPs. Ten subjects (62.5%) lowered their pressure with one topical medication. Two subjects (29-RM and 33-KV) did not use medications because they had sufficient IOP control following filtration surgery. Prostaglandin analogs were the most prescribed drug class (56%) followed by beta blockers (25%), carbonic anhydrase inhibitor/b-blocker combinations (12.5%), and alpha agonists (6.5%).

The control group had a mean IOP of 15.2±2.9 mm Hg in the right eye and 15.1±2.6 mm Hg in the left eye. The POAG group had a mean IOP of 15.31±3 mm Hg in the right eye and 15.4±2.8 mm Hg for the left eye. The difference in IOP between the two groups was not significant. Optic nerve appearances varied greatly depending on the group. In the control group, the mean horizontal cup to disc ratio/vertical cup to disc ratio for the both eyes was 0.34/0.34+0.13. For the POAG group, the values increased to 0.8/0.8+0.18. This difference was statistically significant (p<0.0001).

Visual Fields and Optical Imaging

Threshold visual fields were used to classify subjects into different glaucoma severity groups. Two control subjects (10-SK and 34-JS) completed automated VFs (30-2) because of a positive family history of POAG and optic nerve appearance. These fields were normal for both subjects. As previously mentioned one subject (43-MM) reported a subjective decrease in VA that was not observed by her normal eye exam. The cornea, lens, and macula of subject 43-MM were free of opacities, and the optic nerve was normal in appearance without pallor. However, a 30-2 VF revealed an overall reduced sensitivity in both eyes. Because of the inclusion criteria this subject was tested and included in the normal group. Everyone in the POAG group had visual field defects ranging from nasal steps to double arcuate scotomas in one or both eyes. Everyone in the POAG group also exhibited optic nerve defects as indicated by reduction (damage to) in the neural retinal rim. There was no correlation between the type of VF or nerve fiber defects and foveal sensitivity.

Testing Procedures

After subjects were evaluated, the cone photoreceptor sensitivity test was initiated. No subject failed to complete the test for any reason. Prior to the initiation of the test, the eyes of each subject were anesthetized using Fluress, and IOPs were measured using Goldman tonometry using standardized protocols. One drop of tropicamide (1%) and one drop of phenylephrine (2.5%) were used to dilate the right eyes of the subjects. Once the pupil was no longer reactive to light and dilated to 7 mm in diameter, the subject was ready for cone photoreceptor sensitivity testing. A refraction was performed if the VA of the subject was 20/25 or worse. The subject's best refractive correction was placed on an eyeglass frame by means of a Janelli clip and used for correction during the testing.

A dental impression was made of each subject's upper and lower front teeth with Kerr Type I impression compound while the subject's eye was dilating. The manufacturer's instructions were followed in preparing the dental impression. The finished dental impression was placed on a bite bar which was then mounted onto a fully adjustable microscopic stage on the optical test instrument. The dental impression mounted on the bite bar served to maintain the subject's head stationary during the testing procedure.

Figure 1B:
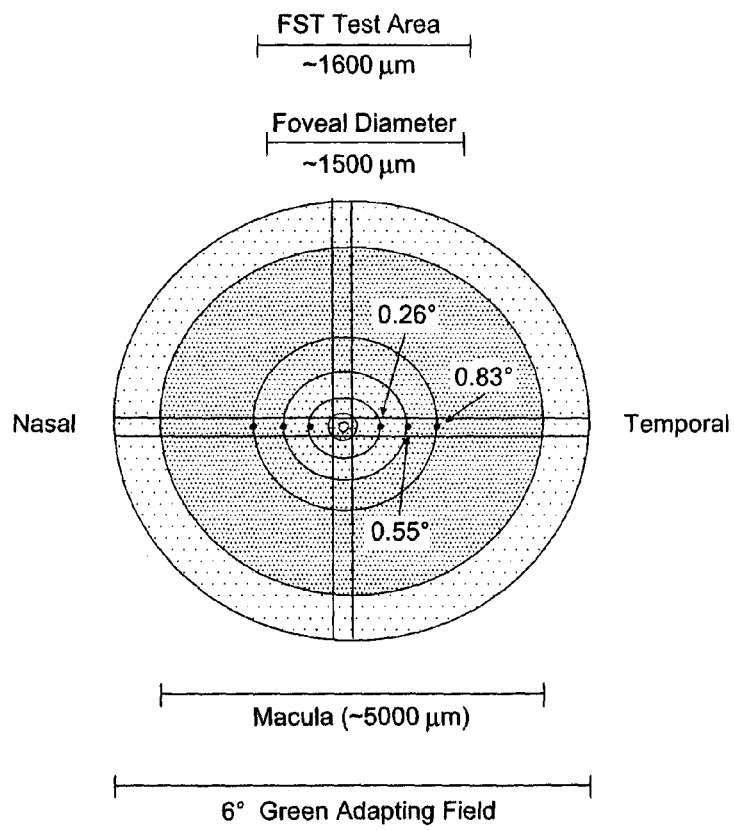
FIG. 1B shows the dimensions of the human macula with foveal sensitivity target image overlay. The subject is instructed to fixate at the square formed at the center of the cross hairs (the fixation target). The white dot in the center of the square is the position of the target image in the foveal center (0 degrees). The black dots show target image positions with temporal and nasal movement of 0.26, 0.55, and 0.83 degrees from the foveal center. In this embodiment, 0.26 degree movement corresponds to 1 mm of movement. The 0.83 degree positions nasal and temporal are at the periphery of the fovea.

During the testing procedure, the subject was presented with a fixation target presented on a larger adapting field as the background. In the testing protocol, the fixation target was a square formed by the intersection of four cross hairs (FIG. 1B). The subject was instructed to look at the center of the square formed by the four cross hairs. Adjustment of the bite bar in the x, y, and z axes was used for alignment with the fixation target and to maintain the subject's eye in the proper eye position. An infrared camera focused on the subject's right pupil was used to monitor eye positions and confirm alignment. The left eye was covered by an eye patch during the test.

After subject alignment, a target image is presented to the subject during testing. The target image is presented to the subject against the adapting field. The adapting field is designed to saturate the rod photoreceptor cells while the target image is designed to stimulate the cone photoreceptor cells. In the testing procedure, the adapting field was a 6 degree continuous adapting field and had an initial luminosity such that the subject could see the target image and an adapting field wavelength of 540 nm. The adapting field wavelength was produced by passing the first light source through a Wratten #58 filter. The target image was a flashing 13 minute circular flash presented for 1/20 of a second (50 milliseconds) every second. The target image has a target image wavelength of greater than or equal to 600 nm. The 540 nm (green) adapting field was chose to be close to the optimal response wavelength of the rod photoreceptors and was used to saturate the response of the rods. The 600 nm or greater (orange-red) target image was used to elicit responses from long wavelength cone photoreceptors. The size of the target image was chosen to reflect the smaller receptive field sizes of the ganglion cells of the foveal cone photoreceptors. If other areas of the eye are tested (such as, but not limited to, the parafovea or fovea) the target size may be adjusted.

The target image was presented to the subject in a predefined sequence to measure cone photoreceptor sensitivity. In the test method used in the following examples, the target image was presented initially in the center of the fixation target, which corresponds to the foveal center of the subject. The target image was subsequently presented at different positions on the fovea to determine cone photoreceptor sensitivity in other areas of the fovea. Specifically, the target image was presented at the foveal center (0 degrees) and at positions of 0.26 degrees, 0.55 degrees and 0.88 degrees (representing the foveal periphery) from the foveal center in the horizontal meridian in both the nasal and temporal direction. In the instrument used in the testing method, 1 mm of movement of the microscopic stage on which the bite bar and dental impression were mounted corresponded to 0.26 degree of movement relative to the center of the fovea. As a result, the target image was presented to the subject 7 times. In this presentation, five of the seven test points (the 0, 0.26 and 0.55 degree target images in the nasal and temporal direction) were within 1,500 μm of the foveal center while two of the seven test points (the 0.88 degree target image in the nasal and temporal direction) were located on the foveal periphery.

For each presentation of the target image, the subject determined at what point the target image is no longer visible to the subject as the luminosity of the adapting field is altered. In the test method used in the examples, the initial luminosity of the adapting field varied depending on the subject (the initial luminosity was selected so that the target image would be visible to all subjects) and the luminosity was increased in 0.1 log units by the subject (by manipulating a computer mouse as described below) until the target image was no longer visible. The point at which the subject indicates the target image is no longer visible is the endpoint measurement for the given target image (the endpoint measurement is expressed as the luminosity of the adapting field). The process was repeated four times for each target image location and the results average to determine a final averaged endpoint measurement for each target image position. The process above for obtaining endpoint measurements was repeated for each location of the target image. The luminosity of the adapting field at which the endpoint measurement was determined.

The endpoint measurements of the subjects in the control and POAG groups were separately analyzed and compared to determine if there were differences in cone photoreceptor sensitivity between the two groups.

The overall testing time varied depending on the subject's cone photoreceptor sensitivity. The total test times ranged from 10 to 30 min. If the cone photoreceptor sensitivity was greatly reduced, there was little difference between the cone photoreceptor sensitivity determined at the foveal center (foveola) and the foveal periphery, and the testing session duration was short. If the cone photoreceptor sensitivity in the foveal center differed greatly from the cone photoreceptor sensitivity in the foveal periphery, the testing session duration was longer. Some subjects required rest breaks during the testing session. The breaks prolonged the overall testing time because the patient had to be carefully repositioned on the bite bar to ensure proper pupil position.

Specific Description of the Apparatus

The following discussion describes a specific embodiment of the apparatus used in the cone photoreceptor sensitivity test described herein. The specific embodiment of the apparatus was used on subjects in order to determine the efficacy of the disclosed method. The following discussion is provided to be exemplary of the general apparatus disclosed and should not be considered to limit the scope of the present disclosure to the specific apparatus disclosed below.

The instrument used in administering the test (FIG. 1) comprised a first and a second light source, which generated a first and a second optical beam. The first and second light sources were tungsten quartz halogen light sources producing white light (Oriel Model #63941 lamps). The first optical beam was used to generate the continuous adapting field which serves as a background and the second optical beam was used to generate a target stimulus, which was presented in a flashing mode. The first and second optical beams were brought together by a beam splitter in Maxwellian view and the collimated optical beams were imaged on the subject's entrance pupil by a lens. The angular subtense at the entrance pupil of the eye was computed by the following formula:

$$\Theta = \frac{c}{f_2} \text{radians} \times \frac{3.44 \times 10^3}{\text{radians}} \text{minutes} \times \frac{1^0}{60 \text{ minutes}} \quad (1)$$

where $\Theta$ is the angular subtense at the entrance pupil, c is the size of the target, and $f_2$ is the secondary focal length of the lens (L1) (18).

The first optical beam traveled through a neutral density wedge filter to control the luminosity (intensity) of the adapting field and a Wratten #58 filter (transmission near 540 nm) to control the wavelength of the adapting field (the adapting field wavelength). The neutral density wedge filter was controllable by the subject using a computer mouse in communication with a standard electronic motor capable of adjusting the neutral density wedge filter. The subject was instructed to press the left button of the mouse to move the neutral density wedge filter to make the adapting field appear brighter. The motor rotated the wedge 0.10 log units each time the button was pressed. The luminance of the adapting field ranged from 0.8 to 65.6 cd/m$^2$ depending on the wedge position. The right button of the mouse was used to reverse the direction of the neutral density wedge filter. The speed of the motor was adjusted to rotate 20 mm/s for all tests. The neutral density wedge filter was calibrated using a Tektronix J18 Lumacolor II photometer. The luminosity of the first optical beam was displayed using a light emitting diode display in increments of 0.0 to 2.0 log units. This combination produced a 6° continuous adapting field of 540 nm (green).

The second optical beam was exposed to the subject intermittently by means of an electronically controlled Uniblitz shutter (the flash had a temporal duration of ¹⁄₂₀ of a second and was exposed to the patient once every second and traveled through a Wratten #25 filter that excludes all wavelengths shorter than 600 nm to produce a orange-red flashing target image. Prism and lenses were adjusted prior to each testing session to ensure that the target image was in the appropriate positions for each subject.

A dental impression was made of each subject's upper and lower front teeth with Kerr Type I impression compound. The finished dental impression was placed on a bite bar which was then mounted on the test apparatus. The dental impression mounted on the bite bar served to maintain the subject's head stationary during the testing procedure. A fixation target, comprising a square formed by the intersection of four cross hairs was also provided and mounted on a microscopic stage adjustable in the x, y and z axes. Microscopic stage mounting of the fixation target (T2) enabled it to be moved eccentrically relative to the center of each subject's fovea. One millimeter of movement in object space was equal to 0.26° movement from the center of fovea. Similarly, 2 mm of movement equaled 0.55° from the foveal center, and 3 mm equaled 0.83°.

The test apparatus also comprised an infrared camera to monitor the position of the subject's eye during the testing procedure. The infrared camera was in communication with a monitor to display the position of the subject's eye to the healthcare provider administering the test. A front silvered mirror was placed in front of the subject's eye to allow the infrared camera to monitor eye position.

Results

Figure 2:
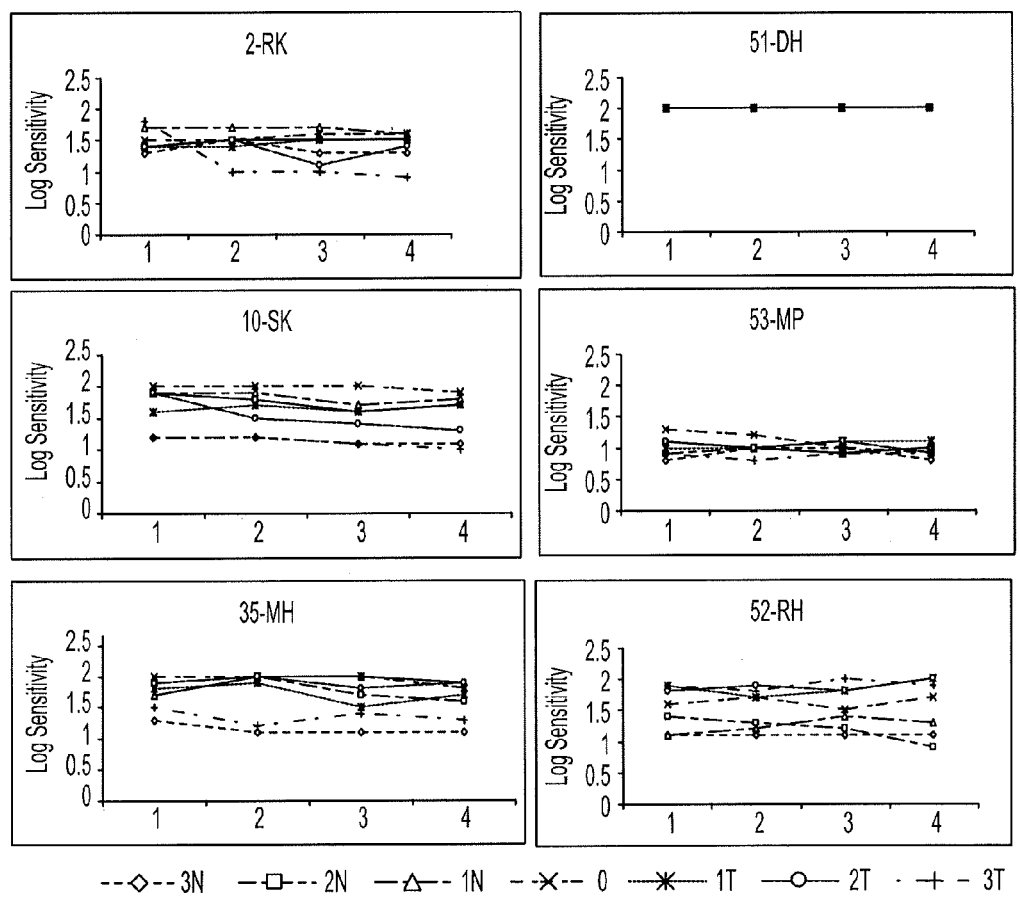
FIG. 2 shows repeated measurements for control group. This is a representative sample for the control group. Each panel shows the graph of the four readings for each foveal position. The 1, 2, 3, and 4 on the x axis are the four times that the subjects were tested at each foveal position. 3N (3 mm nasal), 2N (2 mm nasal), and 1N (1 mm nasal) represent the nasal movement of the target in object in object space. 0 represents the position of the target when at the center of the fovea. 3T (3 mm temporal), 2T (2 mm temporal), and 1T represent the temporal movement of the target in object space. Subject 2-RK had the highest standard deviation (±0.41), whereas 51-DH had the lowest at ±0.
Figure 3:
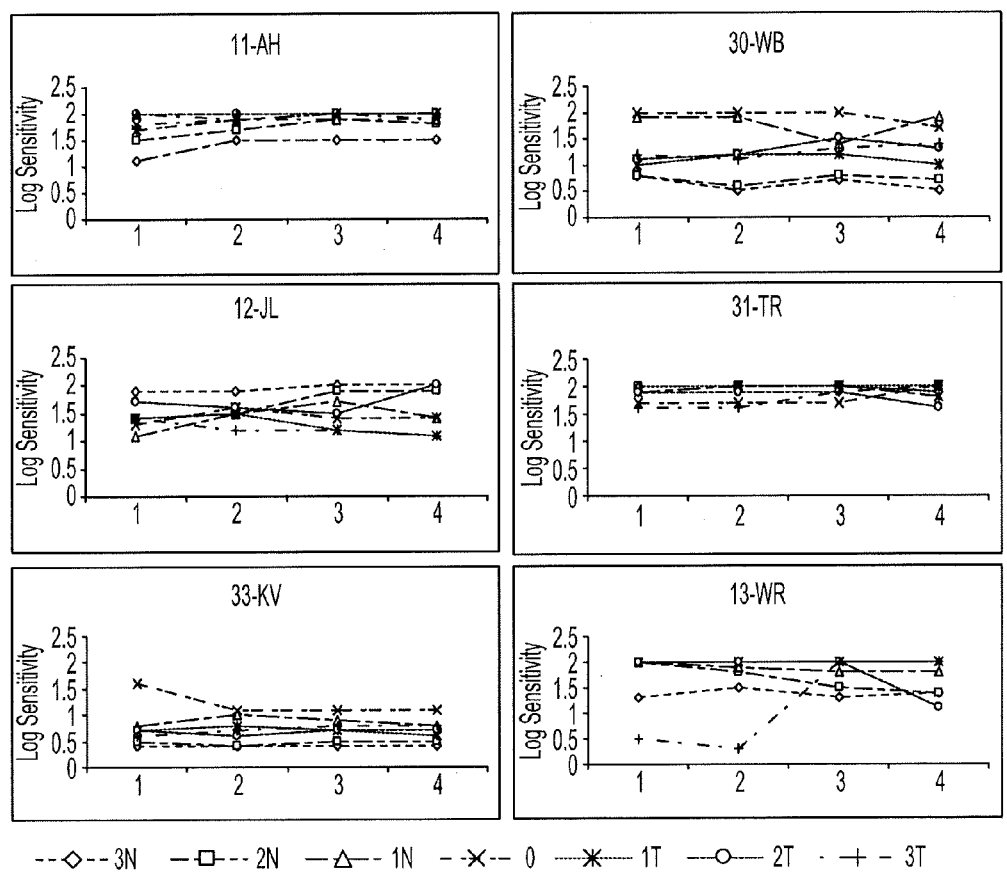
FIG. 3 shows repeated measurements for primary open angle glaucoma group. This is a representative sample of the glaucoma subjects. Each panel shows the graph of the four readings for each foveal position. The 1, 2, 3, and 4 on the x axis are the four times that the subjects were tested at each foveal position. 3N (3 mm nasal), 2N (2 mm nasal, and 1N (1 mm nasal) represent the nasal movement of the target in object in object space. 0 represents the position of the target when at the center of the fovea. 3T (3 mm temporal), 2T (2 mm temporal), and 3T (3 mm temporal) represent the temporal movement of the target in object in object space. Subject 13-WR had the largest variation+0.9 log units. 25-MF had the lowest at +0.12 log units.
Figure 4:
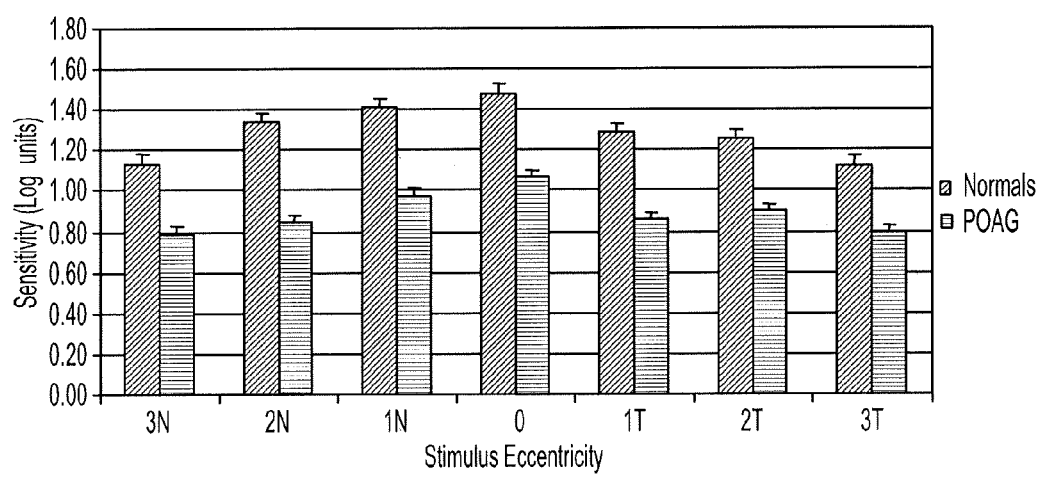
FIG. 4 shows foveal sensitivity by group. This bar graph shows the mean foveal sensitivity for each target image position. 3N (3 mm nasal), 2N (2 mm nasal), and 1N (1 mm nasal) represent the nasal movement of the target in object in object space. 0 represents the position of the target when at the center of the fovea. 3N (3 mm nasal), 2N (2 mm nasal), and 1N (1 mm nasal) represent the nasal movement of the target image in object in object space. 0 represents the position of the target image when at the center of the fovea. 3T (3 mm temporal), 2T (2 mm temporal), and 3T (3 mm temporal) represent the temporal movement of the target image in object space. The error bars shown in the figure are the standard error of the mean (standard deviation/square root of sample) at 95% confidence.
Figure 5:
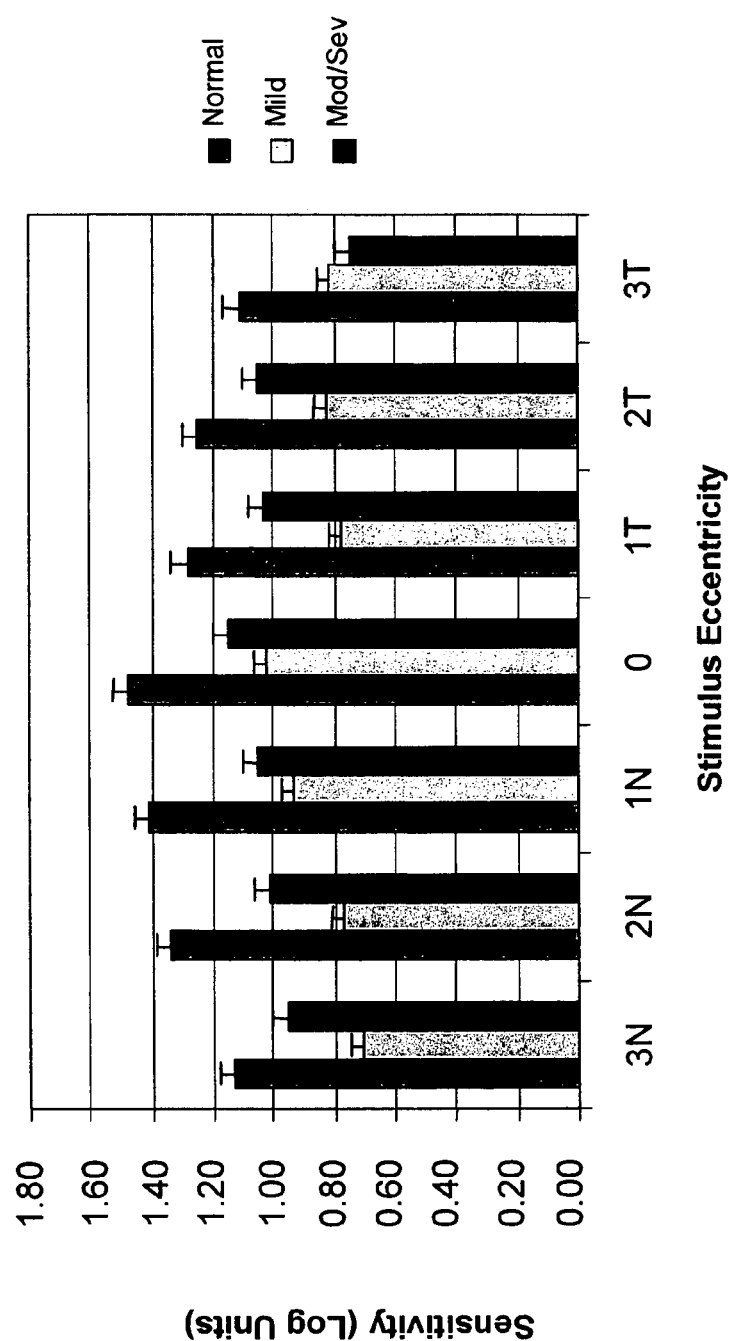
FIG. 5 shows foveal sensitivity by POAG severity. This bar graph shows the mean foveal sensitivity for each target image position for the normal group and those with mild and moderate to severe (Mod/Sev) glaucoma. 3N (3 mm nasal), 2N (2 mm nasal, and 1N (1 mm nasal) represent the nasal movement of the target image in object in object space. 0 represents the position of the target image when at the center of the fovea. 3T (3 mm temporal), 2T (2 mm temporal), and 3T (3 mm temporal) represent the temporal movement of the target image in object space. The error bars shown in the figure are the standard error of the mean (standard deviation/square root of sample) at 95% confidence.

The endpoint measurements obtained at each foveal position tested are shown in FIGS. 2 and 3 for selected patients in the control (FIG. 2) and POAG (FIG. 3 groups). The patient identifier is shown at the tope center of each graph (for example 2-RK) for both the control and POAG groups for each of the 4 endpoint measurements obtained at all 7 foveal positions tested (designated as 0, foveal center, and 1N, 2N and 3N for the 0.26, 0.55 and 0.83 degree nasal position measurements and 1T, 2T and 3T for the 0.26, 0.55 and 0.83 degree temporal position measurements). It is difficult to visually compare these groups using a repeated measures design; therefore, for simplicity they are represented as the average for each testing location for each group. The four endpoint measurements from each subject at a given foveal position tested were first averaged to yield an averaged subject endpoint measurement for that foveal position. Then, the averaged endpoint measurements for that foveal position from all subjects of each group were averaged to yield a group endpoint measurement for that foveal position. Tables 2 and 3 show the mean foveal sensitivities and standard deviations for both control and POAG groups subject to foveal sensitivity testing as described above. FIGS. 4 and 5 show these results graphically. FIG. 4 shows mean foveal sensitivities calculated as described above at each foveal position tested for the control vs. POAG group. FIG. 5 shows mean foveal sensitivities calculated as described above at each foveal position tested with the POAG group further segregated by POAG severity. In FIGS. 4 and 5, 1N, 2N, 3N, 0, 1T, 2T and 3T are as described for FIGS. 2 and 3.

For statistical analysis, the severe and moderate glaucoma subjects were grouped together because there was only one patient with severe glaucoma. The general linear model of repeated measures was used to analyze the data. Using linear regression, the multiple dependent variables (foveal position) can be tested as predictor variables. The model attempts to identify those quantities in systems of equations which are unchanged under linear transformations of the variables in the system. Comparing the group endpoint measurements from the POAG group to the control group for all foveal positions, there was a statistically significant difference between the two groups (p=0.04). The foveal sensitivity of the POAG group was reduced compared to the control group.

Psychophysical tests should be user friendly and reliable. The test/retest and intrasubject reliability for the disclosed foveal sensitivity test was examined. The foveal sensitivity test had good intrasubject reliability regardless of which group (POAG or control) the subject belonged. Because multiple measures were taken on each subject, an average and standard deviation for the measurements at each foveal position could be calculated. The described foveal sensitivity test was easy to understand from the subject's point of view and did not require an experienced observer or a subject experienced in psychophysical testing in order for the measurements obtained to be accurate and repeatable. The standard deviations ranged from 0 to 0.9 for all subjects (Table 4). The legend at the bottom of the figures represents the seven foveal positions. For patient 10-SK in the foveal center (0 position), the standard deviation of the four repeated readings was 0.05. Two normal subjects with VAs of 20/15 had foveal sensitivities that measured 2.0±0 log units at all foveal eccentricities. This increased sensitivity, even in the foveal periphery, may reflect better than normal VA due to increased photoreceptor density. Subject 13-WR had the largest standard deviation value of ±0.9. This subject was an outlier because the next highest standard deviation was ±0.4. Subject 13-WR was also unique in that he was the only monocular patient in the study. An examination of the 13-WR graph in FIG. 3 shows that the largest log unit difference occurred at the 3T position. The patient was repositioned to make sure that the target image was entering the pupil properly and the results were unchanged. The test also had high test-retest reliability. Subject 2-RK was tested on two separate occasions. A dependent t-test showed that there was no statistical difference between the two sets of data.

The present disclosure discloses a newly developed test to determine the function of the cone photoreceptor pathway by measuring the sensitivity of the cone photoreceptors. The newly developed test demonstrated a significant difference (p=0.04) in cone photoreceptor sensitivity in control subjects compared to those subjects with POAG (POAG group). The test is shown to be reliable in people of different ages, with and without glaucoma. The test is easy to understand and simple for inexperienced subjects to learn and to execute. The newly developed test gives researchers and healthcare providers a new tool for expanding our knowledge of the effect of eye disease on the cone photoreceptor pathway. The test also appears to have high potential for diagnosing glaucoma and other eye diseases involving the fovea, parafovea, macula, neurological pathways used by these area to communicate with the visual processing centers in the brain and cone photoreceptors or ganglion cells, at an earlier time than is currently possible.

The observed difference in cone photoreceptor sensitivity showed that on average the control subject had better sensitivity than subjects with mild POAG and the subjects with mild POAG had better sensitivity than those subjects with moderate/severe POAG. Some subjects with moderate POAG had better sensitivity than those subjects with mild group. This could be the result of the type of glaucoma medications (drug class) used. It has been proposed that certain medications have neuroprotective properties (19, 20). However, the effect of medication on cone photoreceptor sensitivity is unknown.

Attempts were made to recruit normal patients for this research at the same location, but most of the patients without glaucoma did not meet the eligibility requirements due to intraocular lens implants or opacities in the crystalline lens. The inclusion criteria used in this study were based on the premise that intraocular lens implants might alter photoreceptor sensitivity. Future studies should recruit phakic and pseudophakic patients to determine if crystalline lens removal affects the foveal sensitivity. A small group of glaucoma suspects (those subjects whose were believed to have very early stages of glaucoma but who did not yet meet the standard diagnostic criteria) were recruited for this study. Due to the size of this group (n=6), the suspects were not included in the statistical analysis. However, the suspects did follow the expected trend where suspects had better cone photoreceptor sensitivity than the POAG group, but worse than the control group.

Figure 6:
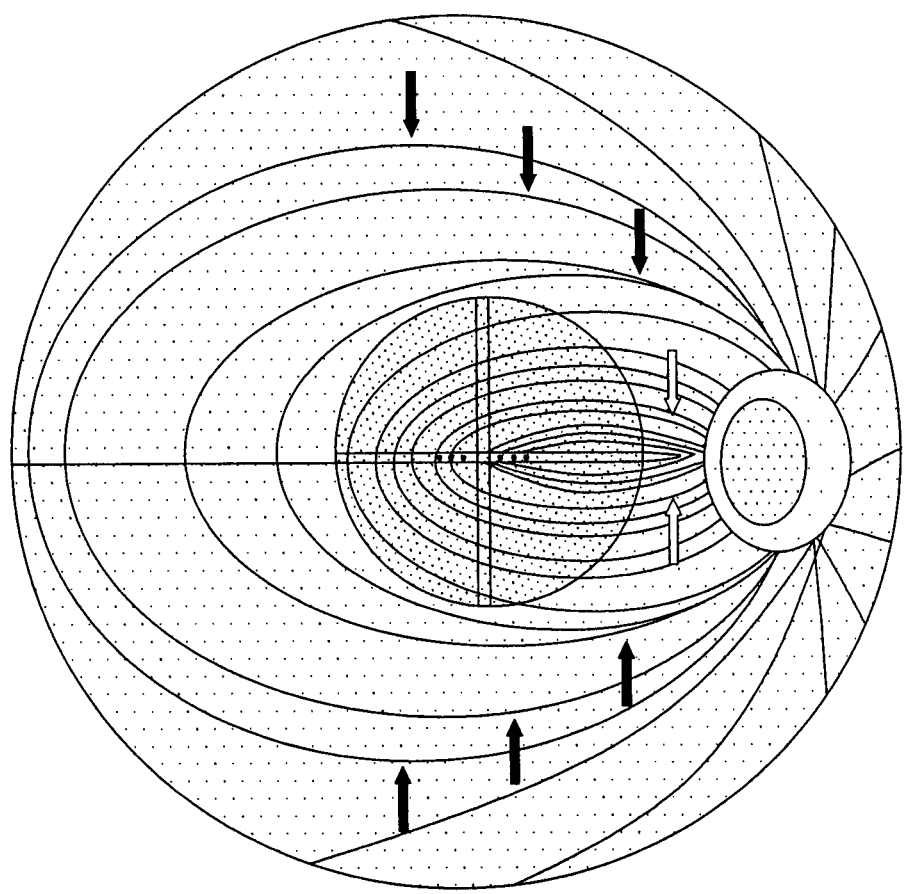
FIG. 6 shows graphically one potential theory of reduced foveal sensitivity in primary open angle glaucoma (POAG) subjects. This is a diagram of the posterior pole of the right eye with the foveal sensitivity test background over the fovea (circle with cross hairs). In the traditional POAG theory, peripheral visual field defects are caused by damage to the peripheral nerve fibers (black arrows). The proposed theory (white arrows) shows an alternate site of damage (papillomacular nerve fiber pathway). This foveal fiber damage could result in reduced foveal sensitivity in the fovea.

The cone photoreceptor sensitivity test may trigger interest in another part of the eye that is often neglected until end stage glaucoma: the fovea. Ganglion cell damage and photoreceptor swelling, damage, and loss have been reported in POAG, but the area of the retina with the highest number of these cells is often neglected. Traditional VF testing methods use targets larger than those used in the current study. A proposed theory for decreased foveal sensitivity in primary open angle glaucoma is shown in FIG. 6. POAG causes damage to the nerve fiber layer which results in peripheral VF (traditional theory) loss. The black arrows show where these damaged nerve fibers are located on the retina. A reduction in cone photoreceptor sensitivity is not observed in early glaucoma or pre-glaucoma subjects with current VF techniques. The proposed theory accounts for how damage to the papillomacular nerve fibers (white arrows) could result in reduced sensitivity of the fovea as seen in the cone photoreceptor sensitivity test.

The foregoing description illustrates and describes the compounds of the present disclosure. Additionally, the disclosure shows and describes only certain embodiments of the methods and apparatus but, as mentioned above, it is to be understood that the teachings of the present disclosure are capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the methods and apparatus disclosed and to enable others skilled in the art to utilize the methods and apparatus disclosed in such, or other, embodiments and with the various modifications required by the particular applications or uses thereof. Accordingly, the description is not intended to limit the methods and apparatus to the forms disclosed herein. All references cited herein are incorporated by reference as if fully set forth in this disclosure. The appended claim is attached solely for the purposes of foreign priority, if needed.

REFERENCES

1. Quigley H A, Vitale S. Models of open-angle glaucoma prevalence and incidence in the United States. *Invest Ophthalmol Vis Sci*. January 1997; 38(1):83-91.
2. Quigley H A. Number of people with glaucoma worldwide. *Br J Ophthalmol*. May 1996; 80(5):389-393.
3. Sommer A, Tielsch J M, Katz J, et al. Racial differences in the cause-specific prevalence of blindness in east Baltimore. *N Engl J. Med*. Nov. 14 1991; 325(20):1412-1417.
4. Lalle P A. Visual Fields. In: Lewis T L, Fingeret M, eds. *Primary Care of the Glaucomas*. New York: Appleton & Lange; 1993:159-208.
5. Quigley H A, Addicks E M, Green W R. Optic nerve damage in human glaucoma. III. Quantitative correlation of nerve fiber loss and visual field defect in glaucoma, ischemic neuropathy, papilledema, and toxic neuropathy. *Arch Ophthalmol*. January 1982; 100(1):135-146.
6. Girkin C A, Emdadi A, Sample P A, et al. Short-wavelength automated perimetry and standard perimetry in the detection of progressive optic disc cupping. *Arch Ophthalmol*. September 2000; 118(9):1231-1236.
7. Porciatti V, Di Bartolo E, Nardi N, Fiorentini A. Responses to chromatic and luminance contrast in glaucoma: a psychophysical and electrophysiological study. *Vision Res*. July 1997; 37(14):1975-1987.
8. Panda S, Jonas J B. Decreased photoreceptor count in human eyes with secondary angle-closure glaucoma. *Invest Ophthalmol Vis Sci*. July 1992; 33(8):2532-2536.
9. Velten I M, Horn F K, Korth M, Velten K. The b-wave of the dark adapted flash electroretinogram in patients with advanced asymmetrical glaucoma and normal subjects. *Br J. Ophthalmol*. April 2001; 85(4):403-409.
10. Werner E B, Krupin T, Adelson A, Feitl M E. Effect of patient experience on the results of automated perimetry in glaucoma suspect patients. *Ophthalmology*. January 1990; 97(1):44-48.
11. Williams Z, Schuman J. Evaluation of the Optic Nerve and Nerve Fiber Layer. In: Rhee D, ed. *Color Atlas and Synopsis of Clinical Glaucoma*. Philadelphia: WB Saunders; 2003:384-417.
12. Nork T M, Ver Hoeve J N, Poulsen G L, et al. Swelling and loss of photoreceptors in chronic human and experimental glaucomas. *Arch Ophthalmol*. February 2000; 118(2):235-245.
13. Greenfield D S, Bagga H, Knighton R W. Macular thickness changes in glaucomatous optic neuropathy detected using optical coherence tomography. *Arch Ophthalmol*. January 2003; 121(1):41-46.
14. Lederer D E, Schuman J S, Hertzmark E, et al. Analysis of macular volume in normal and glaucomatous eyes using optical coherence tomography*1. *American Journal of Ophthalmology*. 2003/6 2003; 135(6):838-843.
15. Curcio C A, Sloan K R, Kalina R E, Hendrickson A E. Human photoreceptor topography. *J Comp Neurol*. Feb. 22 1990; 292(4):497-523.
16. Hodapp E, Parrish R K, Anderson D R. Clinical Decisions in Glaucoma. St. Louis: Mosby; 1993:53.
17. Westheimer G. Dependence of the magnitude of the Stiles-Crawford effect on retinal location. *J Physiol*. September 1967; 192(2):309-315.
18. Westheimer G. The Maxwellian view. *Vision Res*. December 1966; 6(12):669-682.

19. Bautista R D. Glaucomatous neurodegeneration and the concept of neuroprotection. *Int Ophthalmol Clin.* Summer 1999; 39(3):57-70.

20. Schwartz M. Neurodegeneration and Neuroprotection in Glaucoma: Development of a Therapeutic Neuroprotective Vaccine: The Friedenwald Lecture. *Invest. Ophthalmol. Vis. Sci.* Apr. 1, 2003 2003; 44(4):1407-1411.

TABLE 1

Systemic Disease by Group

| Systemic Disease | Controls | POAG |
|---|---|---|
| Hypertension | 47% | 44% |
| African American | 35% | 13% |
| Caucasian | 12% | 31% |
| Diabetes | 17% | 6% |
| African American | 17% | 0% |
| Caucasian | 0% | 6% |
| CVD | 0% | 6% |
| African American | 0% | 0% |
| Caucasian | 0% | 6% |
| Cholesterol | 18% | 13% |
| African American | 18% | 0% |
| Caucasian | 0% | 13% |

TABLE 2

Mean Foveal Sensitivity by Group

| Stimulus Eccentricity | Control n = 17 | | POAG n = 16 | |
|---|---|---|---|---|
| | Mean (log units) | SD | Mean (log units) | SD |
| 3N | 1.13 | ±0.46 | 0.79 | ±0.62 |
| 2N | 1.34 | ±0.51 | 0.85 | ±0.63 |
| 1N | 1.40 | ±0.51 | 0.97 | ±0.53 |
| 0 | 1.48 | ±0.48 | 1.06 | ±0.49 |
| 1T | 1.28 | ±0.53 | 0.85 | ±0.61 |
| 2T | 1.25 | ±0.56 | 0.90 | ±0.58 |
| 3T | 1.12 | ±0.54 | 0.79 | ±0.56 |

Note: SD is the standard deviation. 3N (3 mm nasal), 2N (2 mm nasal), and 1N (1 mm nasal) represent the nasal movement of the target image in object in object space. 0 represents the position of the target image when at the center of the fovea. 3T (3 mm temporal), 2T (2 mm temporal), and 3T (3 mm temporal) represent the temporal movement of the target image in object in object space.

TABLE 3

Mean Foveal Sensitivity by POAG Severity

| Stimulus Eccentricity | Control n = 17 | | Mild POAG n = 11 | | Mod/Sev POAG n = 5 | |
|---|---|---|---|---|---|---|
| | Mean (log units) | SD | Mean (log units) | SD | Mod/Severe (log units) | SD |
| 3N | 1.13 | ±0.46 | 0.71 | ±0.69 | 0.68 | ±0.75 |
| 2N | 1.34 | ±0.51 | 0.77 | ±0.70 | 0.73 | ±0.73 |
| 1N | 1.40 | ±0.51 | 0.93 | ±0.61 | 0.87 | ±0.60 |
| 0 | 1.48 | ±0.48 | 1.02 | ±0.55 | 0.96 | ±0.55 |
| 1T | 1.28 | ±0.53 | 0.77 | ±0.67 | 0.77 | ±0.70 |
| 2T | 1.25 | ±0.56 | 0.82 | ±0.65 | 0.81 | ±0.58 |
| 3T | 1.12 | ±0.54 | 0.81 | ±0.68 | 0.63 | ±0.476 |

Note:
SD is the standard deviation.
3N (3 mm nasal), 2N (2 mm nasal), and 1N (1 mm nasal) represent the nasal movement of the target image in object in object space.
0 represents the position of the target image when at the center of the fovea.
3T (3 mm temporal), 2T (2 mm temporal), and 3T (3 mm temporal) represent the temporal movement of the target image in object in object space.

TABLE 4

Standard Deviations of Repeated Measurements for each Subject

| Patient ID # Control | ‡SD range (log units) | Patient ID # POAG | ‡SD range (log units) |
|---|---|---|---|
| 10-SK | ±0.05 to 0.26 | 11-AH | ±0 to .2 |
| 34-JS | ±0 to 0.17 | 14-DL | ±0.05 to 0.37 |
| 35-MH | ±0.08 to 0.18 | 15-HG | ±0 to .17 |
| 36-IS | ±0 to 0.17 | 16-JW | ±0 to .14 |
| 37-AA | ±0 to 0.33 | 17-WT | ±0.09 to .17 |
| 42-MS | ±0 to 0.14 | 20-JR | ±0 to 0.2 |
| 43-MM | ±0.05 to 0.23 | 24-CM | ±0.05 to 0.2 |
| 44-JS | ±0.05 to 0.18 | 25-MF | ±0.05 to 0.12 |
| 45-GJ | ±0.05 to 0.20 | 29-RM | ±0 to 0.19 |
| 47-WW | ±0.05 to 0.23 | 30-WB | ±0.09 to 0.25 |
| 2-RK | ±0.05 to 0.41 | 31-TR | ±0 to 0.2 |
| 51-DH | ±0 | 12-JL | ±0.05 to 0.26 |
| 52-RH | ±0 to 0.21 | 13-WR | ±0 to 0.9 |
| 53-MP | ±0.05 to 0.18 | 21-GP | ±0.05 to 0.17 |
| 54-CT | ±0 to 0.12 | 28-TC | ±.05 to 0.3 |
| 55-RH | ±0 | 33-KV | ±0 to 0.2 |
| 57-JH | ±0.05 to 0.14 | | |

What is claimed:

1. A method for diagnosing a subject with a disease state or condition by determining a sensitivity of cone photoreceptors in the subject, the method comprising the steps of:
    (a) presenting to a pupil of the subject an adapting field of adjustable intensity to saturate the rod photoreceptors, the adapting field having a single defined wavelength to saturate the rod photoreceptors and an initial intensity selected for the subject such that a target image is either visible or not visible on the adapting field;
    (b) presenting to the pupil of the subject a target image superimposed on an adapting field, the target image having a wavelength selected to stimulate at least one of the blue, green or red cone photoreceptors and the target image being presented at a plurality of locations within about 0.88° of the foveal center of the subject;
    (c) obtaining at least two endpoint measurements, the endpoint measurements being indicative of the sensitivity of the cone photoreceptors from the subject and being obtained by adjusting the intensity of the adapting field in increments until the target image become invisible if the target image was initial visible or until the target image become visible if the target image was initially not visible;
    (d) determining if the sensitivity of the cone photoreceptor is impaired or not impaired based on the endpoint measurement; and
    (e) diagnosing the subject as having a positive disease status if the sensitivity of the cone photoreceptors is impaired or as having a negative disease status if the sensitivity of the cone photoreceptors is not impaired;
    where at least three endpoint measurements are obtained, wherein one of said endpoint measurements is obtained at a foveal center and the remaining endpoint measurements are selected to span the fovea from the foveal center to about 0.88° of the foveal center.

2. The method of claim 1 where the determining step is accomplished by direct inspection of the endpoint measurement obtained from the subject or by comparing the endpoint measurement obtained from the subject to an endpoint measurement determined from a comparison group.

3. The method of claim 2 where the endpoint measurement from the comparison group is contained in a comparative database.

4. The method of claim 3 where the comparison group is diagnosed as having the disease state or condition or diagnosed as being free of the disease state or condition.

5. The method of claim 1 further comprising obtaining an endpoint measurement from a location on the pupil selected from the group consisting of: the fovea, parafovea, macula or a combination of the foregoing.

6. The method of claim 5, comprising obtaining a plurality of additional endpoint measurements, each obtained at a different location on the pupil.

7. The method of claim 6 where the different location is selected from the group consisting of: the fovea, parafovea, macula or a combination of the foregoing.

8. The method of claim 1 where 7 endpoint measurements are obtained, wherein 1 of said endpoint measurements is obtained at a foveal center and the remaining endpoint measurements are selected to span the fovea from the foveal center to about 0.88° from the foveal center.

9. The method of claim 1 where the target image is presented in a continuous or non-continuous manner.

10. The method of claim 9 where the non-continuous manner is a flashing mode, the flashing mode having a flash duration from 1/5 of a second to 1/100 of a second and a flash interval from 10 to 100 milliseconds.

11. The method of claim 1 where the size of the target image is from 5 minutes to 30 minutes.

12. The method of claim 1 where the size of the target image is about 13 minutes.

13. The method of claim 1 where the increment is from 0.05 to 2.0 log units.

14. The method of claim 1 where the initial intensity is from 0.1 to 0.8 cd/m$^2$.

15. The method of claim 1 where the wavelength of the target image and the wavelength of the adapting field are different from one another.

16. The method of claim 15 where the wavelengths of the target image and the adapting field are from about 400 nm to about 700 nm.

17. The method of claim 15 where the wavelength of the target image is greater than about 600 nm and less than about 750 nm and the wavelength of the adapting field is less than about 540 nm.

18. The method of claim 15 where the wavelength of the target image is greater than about 400 nm and less than about 550 nm and the wavelength of the adapting field is greater than about 600 nm.

19. The method of claim 1 where the target image is presented in conjunction with a fixation target.

20. The method of claim 1 where the intensity of the adapting field is adjusted by the subject, by a third party administering the test or automatically.

21. The method of claim 1 where the subject's eye is maintained in a fixed position.

22. The method of claim 1 where a third party monitors the subject's eye to ensure the subject's eye is maintained in a fixed position.

23. The method of claim 1 where said disease state or condition is selected from the group consisting of: age-related macular degeneration, glaucoma, diabetic retinopathy and disease state or condition that impact the macula and/or the central vision of the eye.

24. The method of claim 1 where said disease state or condition is glaucoma.

25. The method of claim 1 where said disease state or condition in primary open angle glaucoma.

26. A method for determining a sensitivity of cone photoreceptors in the subject, the method comprising the steps of:
    (a) presenting to a pupil of the subject an adapting field of adjustable intensity to saturate the rod photoreceptors, the adapting field having a single defined wavelength to saturate the rod photoreceptors and an initial intensity selected for the subject such that the target image is either visible or not visible on the adapting field, size of the target image is about 13 minutes;
    (b) presenting to the pupil of the subject a target image superimposed on an adapting field, the target image having a wavelength selected to stimulate at least one of the blue, green or red cone photoreceptors and the target image being presented at a plurality of locations within about 0.88° of the foveal center of the subject;
    (c) obtaining at least two endpoint measurements, the endpoint measurements being indicative of the sensitivity of the cone photoreceptors from the subject and being obtained by adjusting the intensity of the adapting field in increments until the target image become invisible if the target image was initial visible or until the target image become visible if the target image was initially not visible; and
    (d) determining if the sensitivity of the cone photoreceptor is impaired or not impaired based on the endpoint measurement;

where at least three endpoint measurements are obtained, wherein one of said endpoint measurements is obtained at a foveal center and the remaining endpoint measurements are selected to span the fovea from the foveal center to about 0.88° of the foveal center.

\* \* \* \* \*

UNITED STATES PATENT AND TRADEMARK OFFICE
CERTIFICATE OF CORRECTION

PATENT NO.      : 8,684,946 B1
APPLICATION NO. : 11/641169
DATED           : April 1, 2014
INVENTOR(S)     : Sims et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 447 days.

Signed and Sealed this
Thirtieth Day of May, 2017

Michelle K. Lee
*Director of the United States Patent and Trademark Office*